United States Patent [19]

Gluchowski

[11] Patent Number: 5,066,664
[45] Date of Patent: Nov. 19, 1991

[54] 2-(HYDROXY-2-ALKYLPHENYLAMINO)-OXAZOLINES AND THIAZOLINES AS ANTI-GLAUCOMA AND VASOCONSTRICTIVE AGENTS

[75] Inventor: Charles Gluchowski, Mission Viejo, Calif.

[73] Assignee: Allergan, Inc., Irvine, Calif.

[21] Appl. No.: 486,382

[22] Filed: Feb. 28, 1990

[51] Int. Cl.$^5$ .................. C07D 263/28; A61K 31/42
[52] U.S. Cl. .................................. 514/377; 514/370; 548/190; 548/238
[58] Field of Search ................ 514/370, 377; 548/190, 548/238

[56] References Cited

U.S. PATENT DOCUMENTS

| | | | |
|---|---|---|---|
| 2,027,030 | 1/1936 | Engelmann | 548/190 |
| 2,876,232 | 3/1959 | Bloom | 548/238 |
| 3,432,600 | 3/1969 | Harvey, Jr. | 514/377 |
| 3,453,284 | 7/1969 | Harvey, Jr. | 548/238 |
| 3,598,833 | 8/1971 | Hiltmann et al. | 548/238 |
| 3,624,092 | 11/1971 | Levitt | 548/238 |
| 3,636,219 | 1/1972 | Gulik et al. | |
| 3,679,798 | 7/1972 | Gulik et al. | 514/377 |
| 3,993,766 | 11/1976 | Behner et al. | 514/370 |
| 4,079,144 | 3/1978 | Dürr et al. | 548/190 |
| 4,256,755 | 3/1981 | Smith | 514/377 |
| 4,515,800 | 5/1985 | Cavero et al. | 514/392 |
| 4,587,257 | 5/1986 | DeSantis et al. | 514/392 |
| 4,788,209 | 11/1988 | Baumann | 514/370 |

FOREIGN PATENT DOCUMENTS 0251453 7/1988 European Pat. Off.
1191381 6/1963 Fed. Rep. of Germany.
1195323 6/1963 Fed. Rep. of Germany.

OTHER PUBLICATIONS

Burger, Ed. "Medicinal Chemistry" 2nd Edition, Interscience N.Y. 1960 p. 42.
Wollweber et al. Chem. Abstr. vol. 20 Entry 47428f (1969) abstracting GB 1 132 409.
Sitingare et al. Chem. Abstr. vol. 96 entry 181188T (1982).
Amann et al. Chem. Abstr vol. 78 entry 4237r (1973).

Primary Examiner—Donald G. Daus
Attorney, Agent, or Firm—Gabor L. Szekeres; Robert J. Baran; Martin A. Voet

[57] ABSTRACT

Compounds of the formula

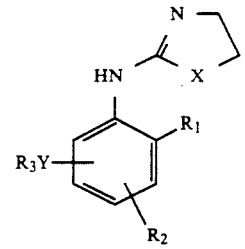

where X is O or S; $R_1$ is lower alkyl having 1 to 6 carbons; $R_2$ is H, lower alkyl having 1 to 6 carbons; or $OR_2^*$ where $R_2^*$ is lower alkyl having 1 to 6 carbons; Y is O, S or NH; and $R_3$ is H, lower alkyl having 1 to six carbons, or $C(O)R_3^*$ where $R_3^*$ is lower alkyl having 1 to 5 carbons, with the proviso that the $YR_3$ group is not disposed in the ortho position on the benzene nucleus relative to the 2-amino group of the oxazoline or thiazoline heterocycle, are active in maintaining or reducing intraocular pressure in the mammalian eye, and are active as vasoconstrictors and capable of reducing or controlling intraocular bleeding of the mammalian eye.

21 Claims, No Drawings

2-(HYDROXY-2-ALKYLPHENYLAMINO)-OXAZOLINES AND THIAZOLINES AS ANTI-GLAUCOMA AND VASOCONSTRICTIVE AGENTS

BACKGROUND OF THE INVENTION

1. Field of the Invention

The present invention is directed to a new class of compounds to wit: to 2-(hydroxy-2-alkylphenylamino)-oxazolines and to 2-(hydroxy-2-alkylphenylamino)-thiazolines which are active as agents for reducing or maintaining intraocular pressure, and also as vasoconstrictors. In another aspect, the present invention is directed to pharmaceutical formulations or compositions which incorporate the novel compounds of the invention. In still another aspect, the present invention is directed to administering such formulations and compositions for reducing or maintaining intraocular pressure (anti-glaucoma) and as vaso-constrictors, for example for controlling ocular bleeding, in mammalian species, including humans.

2. Brief Description of the Prior Art

Compounds useful for reducing or maintaining intraocular pressure are known in the art. Such compounds are used for treating eye diseases which manifest themselves in excessive intraocular pressure, In other words, such compounds are useful for treating glaucoma and related syndromes. That glaucoma is a serious health problem, afflicting approximately 2 per cent of the population over the age of forty years, is well known in medical science.

U.S. Pat. No. 4,515,800, for example, describes the use of 2-(trisubstituted phenylimino)imidazoline compounds [also known as 2-(trisubstituted-anilino)-1,3-diazacyclopentene-compounds] in pharmaceutical compositions, preferably in eye drops, for the treatment of glaucoma.

Another aspect to the background of the present invention is in the field of heterocyclic chemistry, primarily as such chemistry is practiced for the purposes of developing biologically active compounds. In this regard, the following United States and foreign patents, which describe substituted oxazoline, thiazoline and imidazoline compounds, comprise further background to present invention:

U.S. Pat. No. 3,598,833 [2-cycloalkylamino oxazolines having local anesthetic, sedative, vasoconstrictory, mucous membrane de-swelling, blood pressure depressant and gastric fluid secretion inhibitory effects];

U.S. Pat. No. 4,587,257 [2-(trisubstituted phenylimino)imidazoline compounds capable of controlling ocular bleeding];

U.S. Pat. No. 3,636,219 [2-(substituted-phenylamino)-thiazolines and imidazolines having anticholinergic activity];

U.S. Pat. No. 3,453,284 [2-(substituted-anilino)-2-oxazolines;

U.S. Pat. No. 3,432,600 [partially reduced 2-(naphthylamino) oxazolines and indanylamino oxazolines;

U.S. Pat. No. 3,679,798 [compositions comprising arylaminooxazolines and an anticholigeneric agent];

U.S. Pat. No. 3,624,092 [amino-oxazolines useful as central nervous system depressants];

U.S. Pat. No. 2,876,232 [2-(9-fluorenylamino)oxazolines,) and German Patent Nos. 1,191,381 and 1,195,323, and European Patent Application No. 87304019.0.

SUMMARY OF THE INVENTION

This invention covers compounds of Formula 1

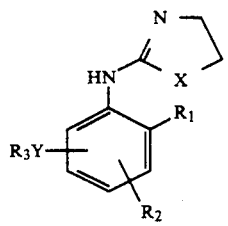

Formula 1 where X is O or S, $R_1$ is lower alkyl having 1 to 6 carbons, $R_2$ is H, lower alkyl having 1 to 6 carbons, or $OR^*_2$ where $R^*_2$ is lower alkyl having 1 to 6 carbons, Y is O, S or NH and $R_3$ is H, lower alkyl having 1 to six carbons, or $C(O)R^*_3$ where $R^*_3$ is lower alkyl having 1 to 5 carbons, with the proviso that the $YR_3$ group is not disposed in the ortho position on the benzene nucleus relative to the secondary amine group of the molecule.

In a second aspect, the present invention relates to the use of the compound of Formula 1 for reducing or maintaining the intraocular pressure in a mammalian eye by administering directly to the mammalian eye a pharmaceutical composition containing an effective amount of one or more compounds of Formula 1. The compounds of Formula 1, or more precisely pharmaceutical compositions containing one or more of such compounds, are particularly useful for treating mammalian, for example human, eyes affected with glaucoma. In this regard the present invention also relates to pharmaceutical formulations comprising one or more compounds of Formula 1 admixed with a pharmaceutically acceptable excipient carrier.

In a third aspect, the present invention also relates to the use of one or more compounds of Formula 1 admixed with suitable pharmaceutical acceptable excipients or carriers, as vasoconstrictors in a mammalian (for example human) species, and particularly as agents for controlling intraocular bleeding.

GENERAL EMBODIMENTS

Definitions

The terms "ester" and "amide" as used here refer to and cover any compound falling within the definition of those terms as classically used in organic chemistry.

The term "alkyl" as used here refers to and includes normal and branch chained alkyl groups as well as cyclo-alkyl groups. The term "lower alkyl", unless specifically stated otherwise, includes normal alkyl, branch chained alkyl as well as cyclo-alkyl groups having 1 to 6 carbon atoms.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of this invention, with reference to Formula 1, are those, where the Ri group is lower alkyl having 1 to 3 carbons, $R_2$ is H or lower alkyl having 1 to 3 carbons, and Y is O. Particularly preferred compounds are those, where X is O, $R_1$ is $CH_3$, $R_2$ is H or $CH_3$ and $R_3$ is H. Generally speaking, between the oxazoline derivatives (X is O) and thiazoline derivatives (X is S), the oxazoline derivatives are preferred.

The most preferred compounds of the inventions are shown as Compounds 1 and 2, respectively.

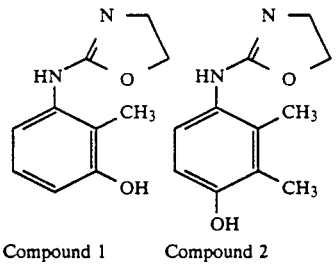

Compound 1    Compound 2

For maintaining intraocular pressure in a mammalian eye, and particularly for reducing such pressure as for treatment of glaucoma in humans suffering from that condition, the compounds of the present invention (or mixtures or salts thereof) are administered to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include water (distilled or deionized water) saline and other aqueous media. The compounds of the invention are preferably soluble in the carrier which is employed for their administration, so that the compounds are administered to the eye in the form of a solution. Alternatively, a suspension of the active compound or compounds (or salts thereof) in a suitable carrier may also be employed.

The compounds of the invention (or mixtures or salts thereof) of) are administered in an ophthalmically acceptable carrier in sufficient concentration so as to deliver an effective amount of the active compound or compounds to the eye. Preferably, the ophthalmic, therapeutic solutions contain one or more compounds of the invention in a concentration range of approximately 0.0001% to approximately 1% (weight per volume) and more preferably approximately 0.05% to approximately 0.5% (weight per volume).

Any method of administering drugs directly to a mammalian eye may be employed to provide the presently useful compound or compounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the presently useful compound or compounds to the mammal's eye is preferably a reduction in intraocular pressure. More preferably, the presently useful compound or compounds are applied topically to the eye or are injected directly into the eye. Particularly useful results are obtained when the compound or compounds are applied topically to the eye.

Topical ophthalmic preparations, for example ocular drops, gels or creams, are preferred because of ease of application, ease of dose delivery, and fewer systemic side effects, such as cardiovascular hypotension. An exemplary topical ophthalmic formulation is shown below in Table I. The abbreviation q.s. means a quantity sufficient to effect the result or to make volume.

TABLE I

| Ingredient | Amount (% W/V) |
|---|---|
| Compound of the invention, for example Compound of Formula 2 or of Formula 3, or mixtures thereof. | about 0.0001 to about 1.0 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

Other excipient components which may be included in the exemplary ophthalmic preparation described in Table I are chelating agents which may be added as needed. The preferred chelating agent is edetate disodium, although other chelating agents may also be used in place of or in conjunction with it.

For treatment of ocular bleeding, which occurs, for example during conventional "invasive" ophtalmic surgery, and also during certain type of ocular surgery conducted with laser, the compounds of the present invention are also administered to the eye in a pharmaceutical composition which comprises, in addition to an effective concentration of one or more compounds of the invention of salts thereof), a suitable, pharmacologically acceptable carrier. Ophthalmic solutions and suspensions are preferred as carriers, and the concentration of the active compound or compounds of the invention may be typically in the same range as for their use as anti-glaucoma agents. The ophthalmic solutions or suspensions are typically adjusted to isotonicity with sodium chloride, and thickening agents such as carboxymethylcellulose, or carbopol may also be employed to enhance delivery. The pH of the ophthalmic solution or suspension is typically also adjusted to be within ophthalmically acceptable range. The specification of U.S. Pat. No. 4,587,257, as it pertains to the utilization of compounds capable of treating or controlling intraocular bleeding, is hereby expressly incorporated by reference.

The anti-glaucoma activity (ability to maintain or reduce intraocular pressure) of the compounds of the present invention was confirmed by the following assay procedure. This assay procedure is generally recognized in the art to provide pertinent information with respect to the anti-glaucoma activity of the formulations assayed. Thus, each of the compounds of the invention to be tested was dissolved in distilled water at a concentration of 0.1% (W/V). Each of these solutions was administered topically and unilaterally to one eye of a drug-naive, unanesthetized New Zealand white rabbit in a single 50 microliter drop. The contralateral eye received an equal volume of saline prior to determining the intraocular pressure after the mixture was administered. Also, approximately 10 microliters of 0.5% (W/V) proparacine (topical anesthetic) was applied to the corneas of each of the rabbits before determining intraocular pressure. As a control test, six (6) other drug-naive, unanesthetized New Zealand white rabbits were treated and tested as described above except that no compound of the invention was included in the solutions administered to the eyes.

The intraocular pressure was determined in both eyes of each rabbit both before and after the solutions were administered. Such intraocular pressure determinations were made in the conventional manner using conventional equipment.

Results of these IOP determinations were as follows:

| Example | Maximum Difference in Intraocular Pressure After Solution Administration mm Hg | |
|---|---|---|
| | Ipsilateral (Treated) Eye | Contralateral (Untreated) Eye |
| Control | N.S. | N.S. |
| Compound 1 | −3.3 ± 1.0 | −7.3 ± 1.0 |
| Compound 2 | −3.9 ± 1.9 | −3.3 ± 0.5 |

N.S. refers to no significant change in the intraocular pressure.

These results demonstrate the effectiveness in reducing intraocular prfesure achieved by directly administering the of the invention to mammalian eyes. In addition, at least with regard to certain mammalian eyes, e.g., New Zealand white rabbit eyes, the intraocular pressure in the contralateral eye is also reduced. When Compound 1 is administered the reduction in the contralateral eye is greater than in the ipsilateral eye.

The vasoconstrictive properties of the compounds of the present invention, i.e. their ability to reduce or control intraocular bleeding, was confirmed by the rabbit aorta: alpha 1 adrenergic receptors in vivo assay procedure, which is recognized in the art to be indicative of the in vivo activity of the tested compounds as vasoconstrictors or as anti intraocular bleeding agents.

Thoracic aorta specimens were obtained form albino rabbits that were killed by $CO_2$ inhalation. The aorta was cut into 3 mm rings. Tissues were placed in Krebs-Hensleit solution of the following composition (millimolar): NaCl 119; KCl 4.7; $MgSo_4$ 1.5, $KH_2 PO_4$ 1.2; $CaCl_2$ 2.5; $NaHCO_3$ 25 and glucose 11.0. The solution also contained cocaine (0.1 millimolar) to block neuronal uptake and EDTA (30 micromolar) and ascorbic acid (5 micromolar) to prevent oxidation of the compound being tested. Tissues were hung in 10 ml organ baths and tension was measured via Grass FTO3 force-displacement transducers. Resting tension was 2 g for the aorta. The solution was gassed with 95% $O_2$ and 5% $CO_2$ and maintained at 37° C. Tissues were allowed to equilibrate for 2 hours before stimulation and the cumulative addition of the compound to be tested (aryl oxazoline) was started. Tissue stimulation was performed using a square wave stimulator (WPI A310) Accupulser with A385 stimulus) at 0.1 Hz, 2 ms pulse width at 90 mA.

The test results of these test with Compound 1 and Compound 2 of the invention, are indicated as follows:

| Rabbit Aorta: Alpha 1 adrenergic receptor assay | |
|---|---|
| | $EC_{50}$ (nm) |
| Compound 1 | 602 ± 108 |
| Compound 2 | 19.9 ± 15.6 |
| L-phenylephrine* | 182 |

*control substance, Shayes and Green; Journal of Pharmacology and Experimental Therapeutics; 1971, Vol-180, pp 317-325

SPECIFIC EMBODIMENTS

The compounds of this invention can be made by a number of different synthetic chemical pathways. To illustrate this invention, there is here outlined a series of steps which have been proven to provide the Compounds of Formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

Thus, the oxazoline derivatives of the present invention (compounds of Formula 1 where X is oxygen) can be made in accordance with the generalized synthetic procedure illustrated in Scheme 1. As a first step, an aniline derivative corresponding to Formula 2 (where the symbols $R_1$, $R_2$ and $YR_3$ are defined as in connection with Formula 1) is reacted Chloroethylisocyanate (Compound 3) which is a commercially readily available reagent. The reaction between compounds of Formula 2 and chloroethylisocyanate (Compound 3) is typically conducted in a neutral solvent, such as tetrahydrofuran (THF) and may be conducted at room temperature or at elevated temperature. In the event the aniline derivative (compound of Formula 2) is added to the reaction as a hydrochloride (or like) salt, an acid acceptor (such as triethylamine) may also be added to the reaction mixture. When the aniline derivative (compound of Formula 2) contains an additional free OH, SH or NH$_2$ group (R$_3$ is H), such hydroxyl, thiol or amino group may be protected by a suitable protective group, although as is apparent from the herein-below provided specific examples, such protection is not necessary when YR$_3$ is OH.

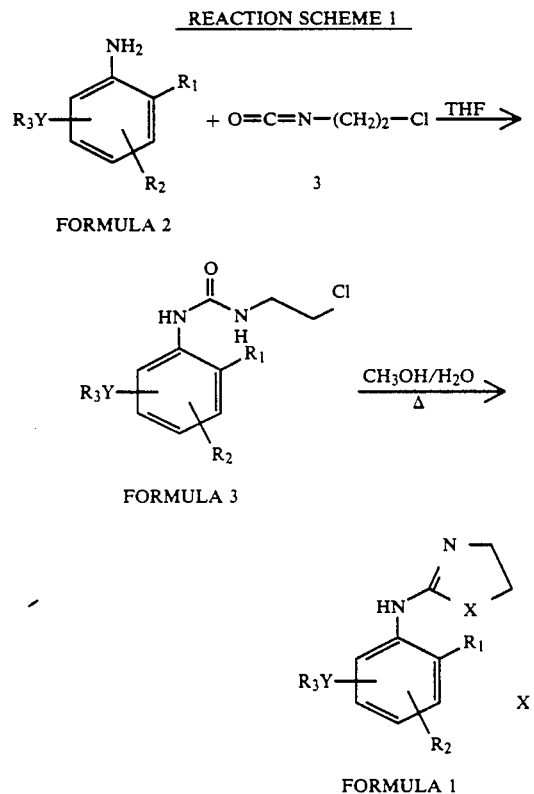

REACTION SCHEME 1

FORMULA 2

FORMULA 3

FORMULA 1

The reaction between chloroethylisocyanate (Compound 3) and the aniline derivative of Formula 2 provides the intermediate chloroethylurea derivative, compound of Formula 3 (R$_1$, R$_2$ and YR$_3$ are defined as in connection with Formula 1). The chloroethylurea derivative (Formula 3) is isolated, for example by evaporation of the reaction medium, and generally speaking, can be adequately characterized and used in the next reaction without further purification.

The chloroethylurea derivative (Formula 3) is cyclized to provide the desired 2-(alkylphenylamino) oxazolines (compounds of Formula 1 where X is oxygen) by heating, preferably in an aqueous medium, such as a solvent mixture containing water and a lower alcohol. Typically, the desired 2-(alkylphenylamino) oxazoline obtained in the cyclization reaction, is isolated from the reaction mixture by first concentrating the same to remove the solvents, and thereafter by recrystallizing the desired product in a suitable solvent or solvent mixture. The desired 2-(alkylphenylamino) oxazolines (compounds of Formula 1 where X is oxygen) may be isolated from the cyclization reaction as the corresponding hydrochloride (or other) salt. In the event a hydroxy, thiol or amino group in the starting aniline derivative (compound of Formula 2) is blocked, the blocking group may be removed after the cyclization reaction in accordance with synthetic steps well known to the practicing organic chemist.

A chloroethylurea derivative (Formula 3) having a free phenolic hydroxyl group, for example, (when YR$_3$ is OH in Formula 3) can be acylated (for example acetylated) on the phenolic hydroxyl group to provide an intermediate 2-chloroethylurea derivative (where YR$_3$ is O-acyl in Formula 3). Such acylated intermediate can also be cyclized to the corresponding 2-(acyloxy-2-alkylphenyl)-oxazolines by heating, in analogy to the above-described cyclization reaction.

Thiazoline derivatives of the present invention (compounds of Formula 1 where X is sulfur) can be made in accordance with the generalized synthetic procedure illustrated in Scheme 2. Thus, an aniline derivative corresponding to Formula 2 (where the symbols R$_1$, R$_2$ and YR$_3$ are defined as in connection with Formula 1) is reacted with chloroethylisothiocyanate (Compound 4). Chloroethylisothiocyanate (Compound 4) like the corresponding isocyanate, is also available commercially. In accordance with Scheme 2, the aniline derivative of Formula 2 (which if necessary may be protected on a hydroxyl, thiol or amino function corresponding to the YR$_3$ moiety) is reacted, usually at room temperature or under mild conditions of heating, with chloroethylisothiocyanate (Compound 4) to provide the intermediate chloroethythiourea derivative (compound of Formula 4). The chloroethythiourea intermediate (compound of Formula 4) is isolated from the reaction and may be cyclized, usually without further purification, by heating in a suitable solvent, preferably in an aqueous solvent system comprising, for example, water and methanol.

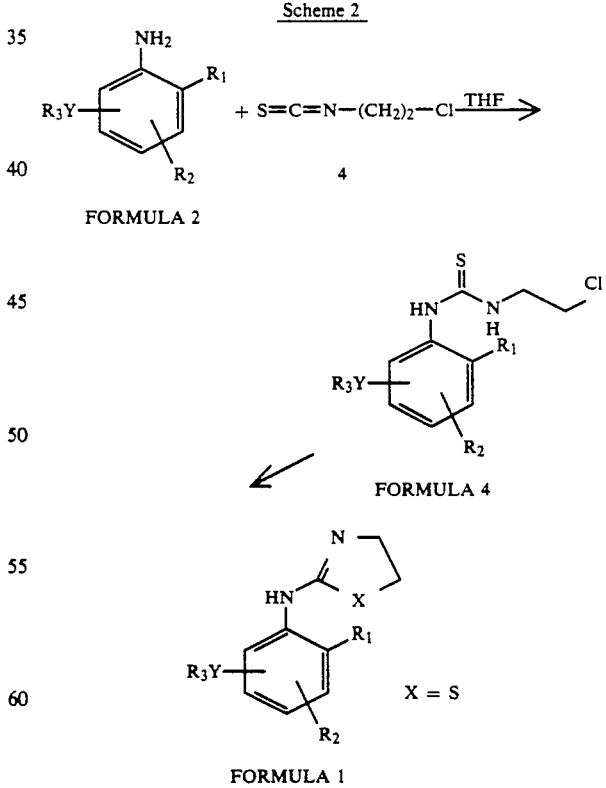

Scheme 2

FORMULA 2

FORMULA 4

FORMULA 1

As in the case of the corresponding oxazoline compounds, the 2-(alkylphenylamino) thiazoline end products (compounds of Formula 1 where X is sulfur) can typically be isolated from the reaction mixture by first concentrating the same to remove the solvents, and therafter by recrystallizing the desired product in a suitable solvent or solvent mixture. The desired 2-(alkylphenylamino) thiazolines (like the corresponding oxazolines) may also be isolated from the cyclization reaction as the corresponding hydrochloride (or other) salt. As in the case of the corresponding oxazolines, any intermediate blocking group may be removed from a hydroxy, thiol or amino function carried by the benzene nucleus, in accordance with synthetic steps well known to the practicing organic chemist.

SPECIFIC EXAMPLES

2-(3-Hydroxy-2-methylphenylamino)-Oxazoline, hydrochloride

Compound 1

Chloroethylisocyanate (Compound 3) 274 mg, 2.6 mmol) was added to a stirred solution of 3-amino-2-methylphenol (Aldrich, 302 mg, 2.45 mmol) in 2 ml of tetrahydrofuran (THF). The reaction mixture was stirred at room temperature for 1.5 hours before concentration in vacuo to yield a black solid. The solid was dissolved in $CH_3OH$, treated with decolorizing carbon, filtered through Celite and concentrated in vacuo to yield 485 mg (87%) of the intermediate chloroethylurea as an off-white solid: mp 139°–141° C., HNMR (300 MHz, $d_6DMSO$ & 9.24 (s, 1H); 7.79 (s, 1H); 7.24 (d, 1H); 6.85 (m, 1H); 6.50 (m, 1H); 3.67 (m, 2H); 3.44 (m, 2H); 2.02 (s, 3H); Mass spectrum m/e 228.0657 ($C_{10}H_{13}ClN_2O_2$ requires 228.0665. The chloroethylurea (158 mg, 0.69 mmol) was suspended in $H_2O$ (2 ml) and $CH_3OH$ (2 ml) and heated to reflux for 1.5 hours before cooling to room temperature and concentration in vacuo to yield a brown residue. The residue was recrystallized from diethylether/$CH_3OH$ to yield 115.4 mg (73%) of the title compound as its hydrochloride salt: mp 148°–150° C.; HNMR (300 MHZ, $d_6DMSO$) & 13.45 (br, 1H); 9.93 (s, 2H); 7.06 (t, 1H); 6.90 (d, 1H); 6.75 (d, 1H); 4.83 (t, 2H); 3.81 (t, 2H); 2.04 (s, 3H); Mass spectrum m/e 228.0657 ($C_{10}H_{13}ClN_2O_2$) requires 228.0665).

Following a substantially similar procedure and starting with the corresponding substituted 3-aminophenol, the following additional examples of compounds of the invention can be synthesyzed:
2-(3-hydroxy-2-ethylphenylamino)-oxazoline;
2-(3-hydroxy-2-propylphenylamino)-oxazoline;
2-(3-hydroxy-2,4-dimethylphenylamino)-oxazoline;
2-(3-hydroxy-2,5-dimethylphenylamino)-oxazoline;
2-(3-hydroxy-2,6-dimethylphenylamino)-oxazoline;
2-(3-hydroxy-2-ethyl-4-methylphenylamino)-oxazoline;
2-(3-hydroxy-2-ethyl-5-methylphenylamino)-oxazoline;
2-(3-hydroxy-2-ethyl-6-methylphenylamino)-oxazoline;
2-(3-hydroxy-2-methyl-4-ethylphenylamino)-oxazoline;
2-(3-hydroxy-2-methyl-5-ethylphenylamino)-oxazoline;
2-(3-hydroxy-2-methyl-6-ethylphenylamino)-oxazoline;
2-(3-hydroxy-2,4,5-trimethylphenylamino)-oxazoline;
2-(3-hydroxy-2,4,6-trimethylphenylamino)-oxazoline;
2-(3-hydroxy-2,5,6-trimethylphenylamino)-oxazoline;

2-(2,3-Dimethyl-4-hydroxyphenylamino)-oxazoline, hydrochloride

Compound 2

Chlorethylisocyanate (Compound 3) (221 mg, 2.1 mmol) was added to a stirred solution of 4-amino-2,3-dimethylphenol, hydrochloride (342 mg, 1.97 mmol) and triethylamine (240 mg, 2.4 mmol) in THF (4 ml) at room temperature. After 1.5 hours the reaction was worked-up by diluting with $CH_2Cl_2$ (10 ml) and washing the organic layer with brine. The organic layer was dried over $MgSO_4$ and concentrated in vacuo to yield 384 mg (80%) of the intermediate chloroethylurea as a lavender solid Mp 142°–146° C.; HNMR (300 MHz, $d_6$-DMSO) & 9.04 (s, 1H); 7.65 (s, 1H); 6.97 (d, 1H); 6.59 (d, 1H); 6.34 (m, 1H); 3.64 (m, 2H); 3.39 (m, 2H); 2.07 (s, 3H); 2.05 (S, 3H); Mass spectrum m/e 242.0810 ($C_{11}H_{15}ClN_2O_2$ requires 242.0822). The chloroethylurea (141 mg, 0.58 mmol) was suspended in $H_2O$ (1 ml) and $CH_3OH$ (1 ml) and heated to reflux for 2.5 hours. The reaction mixture was cooled to room temperature and concentrated in vacuo to yield a solid which was recrystallized from diethylether/$CH_3OH$ to yield 79 mg (56% of the title compound as an off white crystalline solid: mp 175°–179° C.; HNMR (300 MHz, $CDCl_3$) & 7.30 (br, 2H); 6.72 (d, 1H); 6.31 (d, 1H); 4.42 (t, 2H); 3.84 (t, 2H); 2.15 (s, 3H); 2.02 (s, 3H); Mass spectrum m/e 206.1035 ($C_{11}H_{14}N_2O_2$ requires 206.1055).

Following a substantially similar procedure and starting with the corresponding substituted 4-aminophenol, the following additional examples of compounds of the invention can be synthesyzed:
2-(4-hydroxy-2-methylphenylamino)-oxazoline;
2-(4-hydroxy-2-ethylphenylamino)-oxazoline;
2-(4-hydroxy-2-propylphenylamino)-oxazoline;
2-(4-hydroxy-2,5-diemthylphenylamino)-oxazoline;
2-(4-hydroxy-2,6-dimethylphenylamino)-oxazoline:
2-(4-hydroxy-2-ethyl-3-methylphenylamino)-oxazoline;
2-(4-hydroxy-2-ethyl-5-methylphenylamino)-oxazoline;
2-(4-hydroxy-2-ethyl-6-methylphenylamino)-oxazoline;
2-(4-hydroxy-2-methyl-3-ethylphenylamino)-oxazoline;
2-(4-hydroxy-2-methyl-5-ethylphenylamino)-oxazoline;
2-(4-hydroxy-2-methyl-6-ethylphenylamino)-oxazoline;
2-(4-hydroxy-2,3,5-trimethylphenylamino)-oxazoline;
2-(4-hydroxy-2,5,6-trimethylphenylamino)-oxazoline;
2-(4-hydroxy-2,3,6-trimethylphenylamino)-oxazoline;

What is claimed is:

1. A compound of the formula

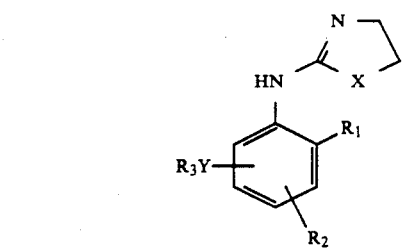

where X is O $R_1$ is selected from a group consisting of straight chain lower alkyl having 1 to 6 carbons and branched chain lower alkyl having only primary, secondary or tertiary carbons adjacent to the phenyl ring and a total of 6 carbons; $R_2$ is selected from a group consisting of H straight chain lower alkyl having 1 to 6 carbons and branched chain lower alkyl having only primary, secondary or tertiary carbons adjacent to the phenyl ring and a total of 6 carbons, or $OR^*_2$ where $R^*_2$ is lower alkyl having 1 to 6 carbons; Y is O, S or NH; and $R_3$ is H, or $C(O)R^*_3$ where $R^*_3$ is lower alkyl having 1 to 5 carbons, with the proviso that the $YR_3$ group is not disposed in ortho position on the benzene nucleus relative to the NH—(C=N—CH$_2$—CH—X) group, and a pharmaceutically acceptable salt thereof.

2. A compound of claim 1 where Y is O.
3. A compound of claim 1 where R$_1$ is lower alkyl having 1 to 3 carbons.
4. A compound of claim 3 where R$_2$ is H or lower alkyl having 1 to 3 carbons.
5. A compound of claim 4 where Y is O.
6. A compound of claim 5 where R$_3$ is H.
7. A compound of claim 4 where Y is S.
8. A compound of claim 7 where R$_3$ is H.
9. A compound of claim 4 where Y is NH.
10. A compound of claim 9 where R$_3$ is H.
11. An intraocular pressure controllant and/or bleeding reducing composition comprising an interocular pressure reducing/maintaining amount or interocular bleeding reducing amount of compound a claim 1 or a pharmaceutically acceptable salt thereof and a pharmaceutically acceptable excipient.
12. A compound of the formula

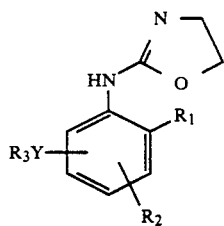

wherein R$_1$ is lower alkyl having 1 to 3 carbons; R$_2$ is H, lower alkyl having 1 to 3 carbons; Y is O, and R$_3$ is H, or C(O)R*$_3$ where R*$_3$ is lower alkyl having 1 to 5 carbons, with the proviso that the R$_2$ and OR$_3$ groups are disposed in the 3 or 4 positions of the benzene nucleus, or a pharmaceutically acceptable salt thereof.
13. A compound of claim 12 wherein the OR$_3$ group is disposed on the 3-position of the benzene nucleus.
14. A compound of claim 12 wherein R$_1$ is CH$_3$.
15. A compound of claim 12 wherein the OR$_3$ group is disposed on the 4-position of the benzene nucleus.
16. A compound of claim 15 wherein R$_1$ is CH$_3$.
17. A compound of the formula

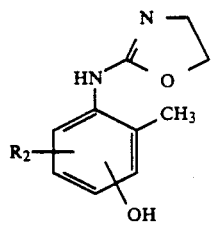

wherein the R$_2$ is H or CH$_3$, and wherein the R$_2$ and OH groups are disposed in the 3 or 4 positions of the benzene nucleus, or a pharmaceutically acceptable salt thereof.
18. The compound of claim 17 wherein the R$_2$ is in the 4-position and is H, and the OH group is in the 3-position, or a pharmaceutically acceptable salt thereof.
19. An interocular pressure controllant and/or bleeding reducing composition comprising an intraocular pressure reducing maintaining amount or intraocular bleeding reducing amount of a compound of claim 18 or a pharmaceutically acceptable salt thereof and a pharmaceutically acceptable excipient.
20. The compound of claim 17 wherein the R$_2$ is in the 3-position and is CH$_3$, and the OH group is in the 4-position, or a pharmaceutically acceptable salt thereof.
21. An intraocular pressure controllant and/or bleeding reducing composition comprising an intraocular pressure reducing/maintaining or intraocular bleeding reducing amount of a compound of claim 20 or a pharmaceutically acceptable salt thereof and a pharmaceutically acceptable excipient.

* * * * *

UNITED STATES PATENT AND TRADEMARK OFFICE
CERTIFICATE OF CORRECTION

PATENT NO. : 5,066,664
DATED : November 19, 1991
INVENTOR(S) : Charles Gluchowski It is certified that error appears in the above-identified patent and that said Letters Patent is hereby corrected as shown below:

IN THE ABSTRACT [57], Line 2 after the formula, after carbons ";" should be —,—;

Column 1, line 47, after "to" insert —the—;

Column 2, line 24, "compound" should be —compounds—;

Column 2, line 36, after "excipient" insert —or—;

Column 3, line 13, "Ri" should be —$R_1$—;

Column 3, line 54, after "thereof)" delete —of)—;

Column 5, line 2, after "invention" insert —(or—;

Column 5, line 58, after "the" (first occurrence) insert —compounds—;

Column 6, lines 43-44, "Compounds" should be —compounds—;

Column 6, line 59, "Chloroethylisocyanate" should be —chloroethylisocyanate—;

Column 10, line 9, "(S," should be —(s,—;

Column 10, line 56, "where" should be —wherein—;

Signed and Sealed this

Fourteenth Day of September, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.  : 5,066,664
DATED       : November 19, 1991
INVENTOR(S) : Charles Gluchowski It is certified that error appears in the above-identified patent and that said Letters Patent is hereby corrected as shown below:

Column 5, line 57, "prfesure" should be —pressure—;

Column 6, line 59, after "reacted" insert —with—;

Column 9, line 45 "synthesyzed" should be —synthesized—;

Column 10, line 26, "synthesyzed" should be —synthesized—;

Column 11, line 18, "of compound a claim" should be —of a compound of claim—.

Signed and Sealed this

Twenty-sixth Day of April, 1994

Attest:

BRUCE LEHMAN

*Attesting Officer*    *Commissioner of Patents and Trademarks*